United States Patent [19]

Heafield et al.

[11] Patent Number: 4,867,985

[45] Date of Patent: Sep. 19, 1989

[54] SPHEROIDS

[75] Inventors: Joanne Heafield; Stewart T. Leslie; Sandra T. A. Malkowska; Philip J. Neale, all of Cambridge, United Kingdom

[73] Assignee: Euroceltique S.A., Luxembourg

[21] Appl. No.: 162,640

[22] Filed: Mar. 1, 1988

[30] Foreign Application Priority Data

Mar. 4, 1987 [GB] United Kingdom ............... 8705083

[51] Int. Cl.$^4$ .............................................. A61K 9/62
[52] U.S. Cl. .................................... 424/461; 424/458; 424/459; 424/488; 424/494
[58] Field of Search .............. 424/488, 489, 458, 469, 424/499, 468, 470, 459, 461, 494

[56] References Cited

U.S. PATENT DOCUMENTS 4,681,765  7/1987  Guley ................................ 424/455

Primary Examiner—Thurman K. Page
Attorney, Agent, or Firm—Nixon & Vanderhye

[57] ABSTRACT

A controlled release pharmaceutical composition contains a number of spheroids, the spheroids containing a water-insoluble drug dispersed in a controlled release matrix. The matrix contains between 70% and 99.5% (by weight) of microcrystalline cellulose, between 0.5% and 4% (by weight) of a cellulose derivative and, optionally, up to 26% of a sugar or a sugar alcohol.

The water insoluble drug must dissolve in water (pH 5) at 20° C. to a concentration of less than 1.0 mg ml−1, preferably less than 0.5 mg ml−1. Preferred drugs are non-steroidal anti-inflammatory agents, especially fenprofen calcium, ibuprofen, ketoprofen, naproxen, diclofenac sodium, fenbufen, flurbiprofen, indomethancin, oxyphenbutazone, phenylbutazone or piroxicam.

17 Claims, No Drawings

SPHEROIDS

The present invention relates to a controlled release pharmaceutical composition containing a water-insoluble drug for administration to humans and/or animals.

In the present specification the term "spheroid" means a spherical granule having a diameter of between 0.5mm and 2.5mm, especially between 0.8mm and 2mm.

In the present context, microcrystalline cellulose is a non-water soluble pharmaceutical excipient that is particularly useful for use in the formation of spheroids by spheronisation. In general terms, the greater the proportion of microcrystalline cellulose present in a pharmaceutical composition, the easier it is to form spheroids. On the other hand, microcrystalline cellulose is an excipient that normally exercises little control over the release of a drug from a dosage form. This means that compositions containing a large proportion of microcrystalline cellulose generally do not exhibit controlled release characteristics.

In the past this problem has been overcome in two ways, either;

(1) The spheroids are coated with a controlled release coating, or (2) The proportion of microcrystalline cellulose is reduced (to about 50% (by weight) or less of total excipient weight), and an excipient that does not exercise control over drug release is added (to a level of about 10% (by weight) or more of total excipient weight).

Both of these solutions have disadvantages. In the first case an extra, uneconomic step is added to the process. In the second case, the reduced level of microcrystalline cellulose often leads to the formation of unsatisfactory spheroids or to difficulties in forming spheroids at all.

The present inventors have now found that controlled-release spheroids containing certain, water-insoluble drugs can be formulated using high levels of microcrystalline cellulose, without the requirement of a controlled release coating.

According to the present invention, therefore, there is provided a controlled release pharmaceutical composition comprising a plurality of spheroids, the spheroids comprising a water-insoluble drug dispersed in a controlled release matrix, wherein the matrix comprises between 70% and 99.5% (by weight) of microcrystalline cellulose and between 0.5% and 4% (by weight) of at least one cellulose derivative.

A "controlled release pharmaceutical composition" according to the present invention is one that achieves slow release of a drug over an extended period of time and extends the duration of drug action over that achieved by conventional delivery. Preferably, such a composition maintains drug level in the blood or target tissue within the therapeutic range for 8 hours or more.

The water-insoluble drug may be any drug that dissolves in water (pH 5) at 20° C. to a concentration of less than 1.0mg ml$^{-1}$, preferably less than 0.5mg ml$^{-1}$. Suitable drugs include benzocaine, nifedipine, bendrofluazide, benzthiazide, chlorothiazide, chlorthalidone, cyclopenthiazide, frusemide, hydrochlorothiazide, hydroflumethiazide, spironolactone, reserpie, chlorpropamide, glibenclamide, betamethasone, cortisone acetate, dexamethasone, hydrocortisone, prednisone, trimethoprim, digoxin, haloperidol, phenytoin, pidolol and clofibrate.

Preferably, however, the water-insoluble drug is a non-steroidal anti-inflammatory agent, such as fenprofen calcium, ibuprofen, ketoprofen, naproxen, diclofenac sodium, fenbufen, flurbiprofen, indomethacin, oxyphenbutazone, phenylbutazone or piroxicam.

The microcrystalline cellulose employed in the present composition may be, for example, Advicel PH 101, or Avicel PH 102, (Trade Marks, FMC Corporation), Emcocel (Trade Mark, Mendell), Elcema (Trade Mark, Degussa).

The cellulose derivative is preferably a cellulose derivative that absorbs water, (a hydratable cellulose) for example, sodium carboxymethyl cellulose. Hydroxy lower alkyl ($C_1$–$C_6$) celluloses, such as hydroxypropyl cellulose or hydroxypropylmethyl cellulose, are especially preferred.

According to one preferred embodiment of the present composition, the weight ratio of the microcrystalline cellulose to the at least one cellulose derivative is between 20:1 and 100:1, especially between 30:1 and 70:1.

In addition to the microcrystalline cellulose and the cellulose derivative, the present controlled release matrix may also comprise other pharmaceutical excipients and diluents that facilitate the formation of spheroids by spheronisation. One particularly suitable further ingredient is a sugar, such as sucrose, dextrose, maltose, or, which is preferred, lactose, or a sugar alcohol, such as mannitol, xylitol or sorbitol.

Preferably, the present matrix contains up to 26% (by weight) of at least one sugar and/or at least one sugar alcohol.

Although it is not necessary in order to achieve controlled release of the drug from the present spheroids, the spheroids may be coated with a suitable film coating in order to, for example, give the spheroids a required colour or to ensure the release of the drug in the intestines rather than the stomach (enteric coating).

A unit dose of the present pharmaceutical composition may consist of, for example, a capsule, a sachet or cachet containing a predetermined quantity of the superoids. The quantity is predetermined by the dose of drug to be incorporated in a unit dose of the composition. Preferred drug doses will be well known to those skilled in the art and include,

| DRUG | AMOUNT OF DRUG PER UNIT DOSE |
|---|---|
| Benzocaine | 10–100 mg |
| Nifedipine | 5–60 mg |
| Bendrofluazide | 0.25–10 mg |
| Benzthiazide | 2–20 mg |
| Chlorothiazide | 50 mg–2 gm |
| Chlorthalidone | 5–200 mg |
| Cyclopenthiazide | 0.1–1.5 mg |
| Frusemide | 2–200 mg |
| Hydrochlorothiazide | 2–100 mg |
| Hydroflumethiazide | 2–200 mg |
| Spironolactone | 5–200 mg |
| Reserpine | 0.1–0.5 mg |
| Chlorpropamide | 50–500 mg |
| Glibenclamide | 2–15 mg |
| Betamethasone | 0.5–5 mg |
| Cortisone acetate | 20–50 mg |
| Dexamethasone | 0.5–15 mg |
| Hydrocortisone | 20–50 mg |
| Prednisone | 1–30 mg |
| Trimethoprim | 50 mg–1 gm |
| Digoxin | 0.05–1 mg |
| Haloperidol | 0.5–10 mg |
| Phenytoin | 25–600 mg |
| Pindolol | 2.5–25 mg |

| DRUG | AMOUNT OF DRUG PER UNIT DOSE |
|---|---|
| Clofibrate | 250 mg–2.0 gm |
| Fenoprofen calcium | 100 mg–1 gm |
| Ibuprofen | 50–800 mg |
| Ketoprofen | 50–200 mg |
| Naproxen | 250–1000 mg |
| Diclofenac Sodium | 25–150 mg |
| Fenbufen | 200–900 mg |
| Flurbiprofen | 50–300 mg |
| Indomethacin | 20–200 mg |
| Oyphenbutazone | 50–250 mg |
| Phenylbutazone | 50–250 mg (human use) |
|  | 500 mg–5 gm (veterinary use) |
| Piroxicam | 10–40 mg |

When a unit dose of the present composition is in the form of a capsule or cachet, the dosage form may be administered directly via the oral route. In the case of a capsule or sachet the spheroids may be sprinkled onto food which is then taken as part of a meal.

The present controlled release pharmaceutical composition may be prepared, in a second aspect of the present invention, by (a) blending a mixture comprising a water-insoluble drug, a predetermined amount of microcrystalline cellulose, a predetermined amount of at least one cellulose derivative and water, (b) granulating and extruding the blended mixture to give a uniform, free-flowing extrudate, (c) spheronising the extrudate until spheroids are formed, (d) drying the spheroids, and (e) optionally, film coating the spheroids, to form a plurality of spheroids, the spheroids comprising a water-insoluble drug dispersed in a controlled release matrix wherein the amounts of the microcrystalline cellulose and the at least one cellulose derivative are so determined that the matrix comprises between 70% and 99.5% (by weight) of microcrystalline cellulose and between 0.5 and 4% (by weight) of at least one cellulose derivative.

Preferably, the spheroids are dried until the moisture content is 5% (by weight) or less of the total spheroid weight (when measured by Karl Fischer titration). Preferably, after drying, in step (d) above, the spheroids are sieved to give spheroids having a predetermined particle size range.

The present composition and process will now be described by way of Example only.

EXAMPLE 1

Phenylbutazone (500gm), microcrystalline cellulose (Avicel PH 102, Trade Mark, 400gm), anhydrous lactose (USP, Spray Dried, 92.5gm) and hydroxypropyl cellulose (Klucel GF, Trade Mark, 7.5gm) were dry mixed. Water (500ml) was then added to form a fairly dense granular mass. The granulated mass was then extruded to form a uniform, free flowing extrudate. The extrudate was sphernoised and the resultant spheroids were dried until they had a moisture content of about 3% (by weight). The dried spheroids were sieved to obtain the 1.0 to 1.4mm diameter sieve fraction.

The in vitro dissolution rate of phenylbutazone from these spheroids using the USP Paddle Method at 100rpm paddle speed, pH 7.5 (USP Buffer), 900ml buffer, at 264nm, is given in Table 1. For comparative purposes, the in vitro dissolution rate of phenylbutazone from normal release Equipaloazone (Trade Mark) granules is also given.

TABLE 1

| | % (by weight) Phenylbutazone Released | |
|---|---|---|
| Hour | "Equipalazone" granules | Example 1 |
| 0.25 | 85.0 | — |
| 0.5 | 96.0 | — |
| 0.75 | 97.6 | — |
| 1 | 100.0 | 34.2 |
| 2 | | 49.1 |
| 4 | | 67.1 |
| 6 | | 78.5 |
| 8 | | 85.6 |
| 10 | | 90.5 |
| 12 | | 93.7 |

EXAMPLE 2

The procedure of Example 1 was followed except that the amount of lactose employed was increased to 95.0gm and the amount of hydroxypropyl cellulose employed was reduced to 5.0gm.

Comparative Example A

The procedure of Example 1 was followed using the following amounts, phenylbutazone (500gm), microcrystalline cellulose (300gm), lactose (150gm) and hydroxypropyl cellulose (50gm). It was found impossible to form spheroids using this formulation as the extrudate was too sticky.

EXAMPLE 3

Indomethacin (220gm), microcrystalline cellulose (Avicel PH 101, Trade Mark, 760gm) and hydroxypropylmethyl cellulose (Methocel E15, Trade Mark, 20gm) were dry mixed. Water (700ml) was then added to form a fairly dense granular mass. The granulated mass was then extruded to form a uniform, free flowing extrudate. The extrudate was sphernoised and the resultant spheroids were dried.

The dried spheroids were then sieved to obtain the 1.0 to 1.4mm diameter sieve fraction.

The dried, sieved spheroids were film coated as follows:

Hydroxypropylmelthyl cellulose (Methocel E5, Trade Mark, 80 gm) was dispersed in water and then mixed until a uniform dispersion was obtained. Opaspray M-1F-6170 (Trade Mark, 50gm) and propylene glycol (5gm) were then added, and the total volume of dispersion was made up to 1 litre by the addition of water. The whole was mixed thoroughly until a uniform dispersion was obtained.

The film coat suspension was then sprayed onto indomethacin spheroids until about 3% (by weight, of the uncoated spheroid weight) film coat solids had been applied.

The in vitro dissolution rate of indomethacin from these film coated spheroids using the USP Paddle Method, 100rpm paddle speed, pH 7.2 (USP Buffer), 900ml buffer volume, at 319nm, is given in Table 2.

TABLE 2

| Hour | % (by weight) Indomethacin released from spheroids prepared according to Example 3 |
|---|---|
| 1 | 16.0 |
| 2 | 22.9 |
| 4 | 31.8 |
| 6 | 38.1 |

TABLE 2-continued

| Hour | % (by weight) Indomethacin released from spheroids prepared according to Example 3 |
|---|---|
| 8 | 43.3 |
| 10 | 47.6 |
| 12 | 51.3 |
| 14 | 54.6 |
| 16 | 57.7 |

Comparative Example B

The procedure of Example 3 was followed except that the starting materials were as follows, indomethacin (200gm), microcrystalline cellulose (Avicel pH 102, 500gm), mannitol (280gm) and hydroxypropylmethyl cellulose (Methocel E15, 20gm).

The spheroids produced were found to release indomethacin too quickly for a controlled release formulation.

EXAMPLE 4

Naproxen (50gm), microcrystalline cellulose (Avicel PH 101, Trade Mark, 48.5gm) and hydroxypropylmethyl cellulose (Methocel E5, Trade Mark, 1.5gm) were dry mixed. Water was then added to form a fairly dense granular mass. The granulated mass was then extruded to form a uniform, free flowing extrudate. THe extrudate was sphernoised and the resultant spheroids were dried.

The dried spheroids were then sieved to obtain the 1.0 to 1.4mm diameter sieve fraction.

The in vitro dissolution rate of naproxen from these film coated spheroids using the USP Paddle Method, 100rpm paddle speed, pH 7.2 (USP Buffer), 900ml buffer volume, at 319nm is given in Table 3.

TABLE 3

| Hour | % (by weight) Naproxen released from spheroids prepared according to Example 4. |
|---|---|
| 1 | 40.8 |
| 2 | 55.9 |
| 3 | 66.4 |
| 4 | 72.6 |
| 5 | 80.1 |
| 6 | 84.4 |
| 8 | 91.6 |
| 10 | 94.9 |

What we claim:

1. A controlled release pharmaceutical composition comprising a plurality of spheroids, the spheroids comprising a water-insoluble drug selected from the group consisting of benzocaine, nifedipine, bendrofluazide, benzthiazide, chlorothiazide, chlorthalidone, cyclopenthiazide, frusemide, hydrochlorothiazide, hydroflumethiazide, spironolactone, reserpine, chlorpropamide, glibenclamide, betamethasone, cortisone acetate, dexamethasone, hydrocortisone, prednisone, trimethoprim, digoxin, haloperidol, phenytoin, pindolol, clofibrate, fenoprofen calcium, ibuprofen, ketoprofen, naproxen, diclofenac sodium, fenbufen, flurbiprofen, indomethacin, oxyphenbutazone, phenylbutazone, prioxicam, dispsersed in a controlled release matrix, whereinthe matrix comprises between 70% and 99.5% of microcrystalline cellulose and between 0.5% and 4% of at least one cellulose derivative.

2. A composition according to claim 1 wherein the water-insoluble drug comprises a non-steroidal anti-inflammatory agent.

3. A composition according to claim 2 wherein the water-insoluble drug comprises at least one of fenprofen calcium, ibuprofen, ketoprofen, naproxen, diclofenac sodium, fenbufen, flurbiprofen, indomethacin, oxyphenbutazone, phenylbutazone and piroxicam.

4. A composition according to claim 3 wherein the water-insoluble drug comprises naproxen.

5. A composition according to claim 3 wherein the water-insoluble drug comprises indomethacin.

6. A composition according to claim 1 wherein the at least one cellulose derivative comprises a hydratable cellulose.

7. A composition according to claim 6 wherein the at least on cellulose drivative comprises a hydroxy lower alkyl cellulose.

8. A composition according to claim 7 wherein the at least one cellulose derivative comprises at least one of hydroxypropylcellulose and hydroxypropylmethyl cellulose.

9. A composition according to claim 1 wherein the ratio of the microcrystalline cellulose to the at least one cellulose derivative is between 20:1 and 100:1.

10. A composition according to claim 9 wherein the ratio is between 30:1 and 70:1.

11. A composition according to claim 1 wherein the controlled release matrix further comprises at least one sugar or at least one sugar alcohol.

12. A composition according to claim 11 wherein the sugar comprises lactose.

13. A composition according to claim 11 wherein the controlled release matrix contains up to 26% (by weight) of at least one sugar or at least one sugar alcohol.

14. A controlled release pharmaceutical composition according to claim 1 in unit dosage form.

15. A composition according to claim 14 in the form of a capsule, cachet of sachet.

16. A process for the preparation of a controlled release pharmaceutical composition according to claim 1 comprising
(a) blending a mixture comprising a water-insoluble drug, a predetermined amount of microcrystalline cellulose, a predetermined amount of at least one cellulose derivative and water,
(b) granulating and extruding the blended mixture to give a uniform, free-flowing extrudate,
(c) spheronising the extrudate until spheroids are formed,
(d) drying the spheroids, and
(e) optionally, film coating the spheroids, to form a plurality of spheroids, the spheroids comprising a water-insoluble drug dispersed in a controlled release matrix wherein the amounts of the microcrystalline cellulose and the at least one cellulose derivative are so determined that the matrix comprises between 70% and 99.5% by weight of microcrystalline cellulose and between 0.5% and 4% by weight of at least one cellulose derivative.

17. A process according to claim 16 wherein the spheroids are dried until the moisture content is between 0% and 5% of the total spheroid weight.

* * * * *